US007214671B2

(12) United States Patent
DeLuca et al.

(10) Patent No.: US 7,214,671 B2
(45) Date of Patent: May 8, 2007

(54) USE OF 2-METHYLENE-19-NOR-20(S)-1α,25-DIHYDROXYVITAMIN D$_3$ FOR THE PROPHYLAXIS OF BONE DISEASES

(75) Inventors: Hector F. DeLuca, Deerfield, WI (US); Lori A. Plum, Madison, WI (US); Margaret Clagette-Dame, Deerfield, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/782,337

(22) Filed: Feb. 19, 2004

(65) Prior Publication Data

US 2005/0187201 A1 Aug. 25, 2005

(51) Int. Cl.
A61K 31/59 (2006.01)
A61K 31/592 (2006.01)
A61K 31/593 (2006.01)
A61K 401/00 (2006.01)

(52) U.S. Cl. ...................... 514/167; 552/653
(58) Field of Classification Search ................ 514/167; 552/653, 167
See application file for complete search history.

(56) References Cited

U.S. PATENT DOCUMENTS

| | | | |
|---|---|---|---|
| 4,777,163 A | 10/1988 | Bosies et al. | |
| 5,587,497 A | 12/1996 | DeLuca et al. | |
| 5,843,928 A * | 12/1998 | Deluca et al. | 514/167 |
| 5,972,917 A * | 10/1999 | Bishop et al. | 514/167 |
| 6,277,837 B1 * | 8/2001 | DeLuca et al. | 514/167 |
| 6,313,103 B1 | 11/2001 | Peyman et al. | |
| 6,316,642 B1 * | 11/2001 | DeLuca et al. | 552/653 |
| 6,369,099 B1 * | 4/2002 | DeLuca et al. | 514/449 |
| 6,392,071 B1 * | 5/2002 | DeLuca et al. | 552/653 |
| 6,440,953 B1 * | 8/2002 | DeLuca et al. | 514/167 |
| 6,458,827 B2 * | 10/2002 | DeLuca et al. | 514/449 |
| 6,482,812 B2 * | 11/2002 | DeLuca et al. | 514/167 |
| 6,506,912 B2 * | 1/2003 | DeLuca et al. | 549/449 |
| 6,537,981 B2 * | 3/2003 | DeLuca et al. | 514/167 |
| 6,566,352 B1 * | 5/2003 | DeLuca et al. | 514/167 |
| 6,638,540 B2 | 10/2003 | Mühlbauer | |
| 6,696,431 B2 * | 2/2004 | DeLuca et al. | 514/167 |

FOREIGN PATENT DOCUMENTS

WO 02/05823 * 1/2002 ............ 31/59

OTHER PUBLICATIONS

Boris et al, "Relative Activities of Some Metabolites and Analogs of Cholecalciferol in Stimulation of Tibia Ash Weight in Chicks Otherwise Deprived of Vitamin D," Vitamin D Metabolites, Analogs and Bone Ash, 1976, pp. 194-198.
Hedlund et al, "Increased Incidence of Hip Fracture in Osteoporotic Women Treated with Sodium Fluoride," Journal of Bone and Mineral Research, vol. 4, No. 2, 1989, pp. 223-225.
Holick et al, Harrison's Principle of Internal Medicine, 13th Ed. 1994, pp. 2137-2151.

Jensen et al, "Treatment of Post Menopausal Osteoporosis, A Controlled Therapeutic Trial Comparing Oestrogen/Gestagen, 1,25-Dihydroxy-Vitamin D-3 and Calcium," Clinical Endocrinology, 16, 1982, pp. 515-524.
Meunier, "Evidence-Based Medicine and Osteoporosis: A Comparison of Fracture Risk Reduction Data from Osteoporosis Randomised Clinical Trials," IJCP, vol. 53, No. 2, Mar. 1999.
Nordin et al, "The Metabolic Basis of Osteoporosis," Osteoporosis: Physiological Basis, Assessment, and Treatment, Elsevier Science Publishing Co., Inc., 1990, pp. 23-36.
Ott et al, "Calcitriol Treatment is not Effective in Postmenopausal Osteoporosis," Annals of Internal Medicine, vol. 110, No. 4, Feb. 15, 1989, pp. 267-274.
Peck, "The Pathogenesis of Postmenopausal Osteoporosis," Osteoporosis: Physiological Basis, Assessment, and Treatment, Elsevier Science Publishing Co., Inc., 1990, pp. 3-6.
Riggs et al, "Bone Turnover Matters: The Raloxifene Treatment Paradox of Dramatic Decreases in Vertebral Fractures without Commensurate Increases in Bone Density," Journal of Bone and Mineral Research, vol. 17, No. 1, 2002, pp. 11-13.
Riggs et al, "Causes of Age-Related Bone Loss and Fractures," Osteoporosis: Physiological Basis, Assessment, and Treatment, 1990, pp. 7-16.
Christensen, Abstract PMID: 6795047, "Effect of 1,25-Dihydroxy-Vitamin D3 in Itself or Combined with Hormone Treatment in Prevent Postmenopausal Osteoporosis," Eur. J. Clin. Invest., Aug. 11, 1981, vol. 11, No. 4.
Klein, "Nutritional Rickets and Osteomalacia," Primer on the Metabolic Bone Diseases and Disorders of Mineral Metabolism, 1996, pp. 301-305.
Kleerekoper, "Treatment of Osteoporosis with Sodium Fluoride Alternating with Calcium and Vitamin D," Osteoporosis: Recent Advances in Pathogenesis and Treatment, 1981, pp. 441-448.
Sarkar, "Relationships Between Bone Mineral Desnity and Incident Vertebral Fracture Risk with Raloxifene Therapy," Journal of Bone and Mineral Research, vol. 17, No. 1, 2002, pp. 1-10.
Cummings et al, "Improvement in Spine Bone Desity and Reduction in Risk of Vertebral Fractures During Treatment with Antiresorptive Drugs," The American Journal of Medicine, vol. 112, 2002, pp. 281-289.
Sudhaker Rao et al, "Metabolic Bone Disease in Gastrointestinal Hepatobiliary, and Pancreatic Disorders," Primer on the Metabolic Bone Diseases and Disorders of Mineral Metabolism, 1996, pp. 306-311.
Watts et al, "Intermittent Cyclical Etidronate Treatment of Postmenopausal Osteoporosis," The New England Journal of Medicine, vol. 323, No. 2, Jul. 12, 1990, pp. 73-79.
Harris, "Four-Year Study of Intermittent Cyclic Etidronate Treatment of Postmenopausal Osteoporosis: Three Years of Blinded Therapy Followed by One Year of Open Therapy," The American Journal of Medicine, vol. 95, Dec. 1993, pp. 557-567.

* cited by examiner

Primary Examiner—Sabiha N. Qazi
(74) Attorney, Agent, or Firm—Andrus, Sceales, Starke & Sawall, LLP

ABSTRACT

(57)
This invention provides pharmaceutical uses for 2-methylene-19-nor-20(S)-1α,25-dihydroxyvitamin D$_3$. This compound is characterized by high bone calcium mobilization activity demonstrating preferential activity on bone. This results in a novel therapeutic agent for the treatment and prophylaxis of diseases where bone formation is desired, particularly osteoporosis. This compound also increases both breaking strength and crushing strength of bones evidencing use in conjunction with bone replacement surgery such as hip and knee replacements, as well as use by normal subjects when high bone mass is desired.

11 Claims, 16 Drawing Sheets

USE OF 2-METHYLENE-19-NOR-20(S)-1α,25-DIHYDROXYVITAMIN $D_3$ FOR THE PROPHYLAXIS OF BONE DISEASES

BACKGROUND OF THE INVENTION

This invention relates to vitamin D compounds, and more particularly to pharmaceutical uses for 2-methylene-19-nor-20(S)-1α,25-dihydroxyvitamin $D_3$.

The natural hormone, 1α,25-dihydroxyvitamin $D_3$ and its analog in ergocalciferol series, i.e. 1α,25-dihydroxyvitamin $D_2$ are known to be highly potent regulators of calcium homeostasis in animals and humans, and more recently their activity in cellular differentiation has been established, Ostrem et al., Proc. Natl. Acad. Sci. USA, 84, 2610 (1987). Many structural analogs of these metabolites have been prepared and tested, including 1α-hydroxyvitamin $D_3$, 1α-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases as renal osteodystrophy, vitamin D-resistant rickets, osteoporosis, psoriasis, and certain malignancies.

Another new class of vitamin D analogs, i.e. the so called 19-nor-vitamin D compounds, are characterized by the replacement of the A-ring exocyclic methylene group (carbon 19), typical of the vitamin D system, by two hydrogen atoms. Biological testing of such 19-nor-analogs (e.g., 1α,25-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Lett. 31, 1823 (1990); Perlman et al., Tetrahedron Lett. 32, 7663 (1991), and DeLuca et al., U.S. Pat. No. 5,086,191).

In U.S. Pat. No. 4,666,634, 2β-hydroxy and alkoxy (e.g., ED-71) analogs of 1α,25-dihydroxyvitamin $D_3$ have been described and examined by Chugai group as potential drugs for osteoporosis and as antitumor agents. See also Okano et al., Biochem. Biophys. Res. Commun. 163, 1444 (1989). Other 2-substituted (with hydroxyalkyl, e.g., ED-120, and fluoroalkyl groups) A-ring analogs of 1α,25-dihydroxyvitamin $D_3$ have also been prepared and tested (Miyamoto et al., Chem. Pharm. Bull. 41, 1111 (1993); Nishii et al., Osteoporosis Int. Suppl. 1, 190 (1993); Posner et al., J. Org. Chem. 59, 7855 (1994), and J. Org. Chem. 60, 4617 (1995)).

Recently, 2-substituted analogs of 1α,25-dihydroxy-19-nor-vitamin $D_3$ have also been synthesized, i.e. compounds substituted at 2-position with hydroxy or alkoxy groups (DeLuca et al., U.S. Pat. No. 5,536,713), which exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, an analog which is characterized by the presence of a methylene substituent at the carbon 2 (C-2) has been synthesized and tested. Of particular interest is the analog which is characterized by the unnatural configuration of the methyl group at carbon 20 (C-20), i.e. 2-methylene-19-nor-20(S)-1α,25-dihydroxyvitamin $D_3$. This vitamin D analog is disclosed in DeLuca et al U.S. Pat. No. 5,843,928, and its use for treating a metabolic bone disease where it is desired to maintain or increase bone mass is taught therein.

As is commonly accepted, human bones are subject to a constant and dynamic remodeling process which includes bone resorption and bone formation. Bone resorption is based on the destruction of bone matrix, and is controlled by specialized cells known as osteoclasts. Bone formation is accomplished by bone forming cells known as osteoblasts which function to replace the bone resorbed by the osteoclasts.

From childhood through adolescence (i.e. up to about age 20), bone modeling and remodeling is controlled so that skeletal growth is at an accelerated pace in order to match the growth of other body organs. Skeletal accumulation continues through young adulthood (from about age 20 to about age 30) though at a slower rate. In normal healthy mature adults (between the ages of about 30 and about 50 (and in the absence of being pregnant for women) the bone remodeling process will typically be at equilibrium between bone formation and bone resportion. Thereafter, and as the normal consequence of aging, an imbalance in the bone remodeling process develops, resulting in loss of bone. If such imbalance continues over time, bone mass and consequently bone strength is reduced leading to increased potential for fractures.

The majority of metabolic bone diseases are based on an imbalance in the remodeling process, i.e. a disturbed equilibrium between bone resorption and bone formation either from an acceleration of bone resorption activity by osteoclasts or reduction in bone formation activity by osteoblasts. In either event, the result is a decrease in the amount of bone mass and a consequent decrease in bone strength, which ultimately develops into a bone disorder or bone disease. The most common metabolic bone disease is osteoporosis. Osteoporosis is a disease characterized by low bone mass and high bone fragility resulting in an increased risk of fractures. It results from an imbalance in the ongoing bone remodeling process, and due to the extremely complex nature of the remodeling process, it is not easily stopped or reversed.

Osteoporosis can develop as a result of numerous different causes. It is generally categorized as including osteoporosis induced by hormone deficiency (e.g. estrogen deficiency commonly referred to as postmenopausal osteoporosis) and old age (e.g. senile osteoporosis) as well as acquired osteoporosis induced by various drug therapies (e.g. steroid induced osteoporosis as a result of treatment with anti-inflammatory glucocorticoid drugs) and what is referred to as low bone turnover osteoporosis.

Conventional osteoporosis treatment includes, for example, the administration of estrogens, estrogen/progesterone (referred to as hormone replacement therapy), calcitonin, vitamin D analogs, bisphosphonates, parathyroid hormone, and sodium fluoride. Each of such treatments has its limitations due to the multifaceted and complex nature of osteoporosis. In addition, some of such treatments involve serious undesirable side effects which limit their utility.

Osteoporosis, and other diseases characterized by a need to increase the strength of a bone, occur with increasing frequency as humans age, especially after middle age. These types of diseases are some of the most important medical disorders affecting the elderly, and because of the high incidence of fractures and their relatively high costs, their prevention remains one of the major unresolved public health problems facing society. Because bone loss has occurred over many years, and possibly decades, before fractures begin to occur, any drug intervention program aimed at preventing the development of metabolic bone diseases such as osteoporosis should begin earlier rather than later in one's life.

SUMMARY OF THE INVENTION

The present invention is directed toward 2-methylene-19-nor-20(S)-1α,25-dihydroxyvitamin D₃, (hereinafter also referred to as 2MD) its biological activity, and various pharmaceutical uses for this compound.

Structurally this 19-nor analog is characterized by the general formula I shown below:

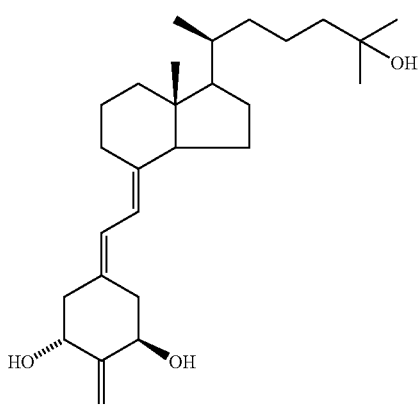

The solid wedge-shaped line to the methyl substituent at C-20 indicates that carbon 20 has the S configuration.

The above compound (2MD) exhibits a desired, and highly advantageous, pattern of biological activity. 2MD is characterized by intestinal calcium transport activity, similar to that of 1α,25-dihydroxyvitamin D₃, but exhibits very high activity, as compared to 1α,25-dihydroxyvitamin D₃, in its ability to mobilize calcium from bone. The latter finding indicates that 2MD shows preferential activity on osteoblasts (bone forming cells) confirmed by direct osteoblast culture experiments (Shevde et al., Proc. Natl. Acad. Sci. USA 99, 13487 (2002)). Hence, 2MD is highly specific in its activity. Its preferential activity on mobilizing calcium from bone allows the in vivo administration of 2MD for the treatment and prophylaxis of metabolic bone diseases where bone loss is a major concern. Because of its preferential activity on bone, 2MD would be a preferred therapeutic agent for the treatment and prophylaxis of diseases where bone formation is desired, such as osteoporosis, especially low bone turnover osteoporosis, steroid induced osteoporosis, senile osteoporosis or postmenopausal osteoporosis, as well as osteomalacia. The administration of 2MD for the treatment and prophylaxis of such diseases may be transdermal, oral or parenteral. 2MD may be present in a composition in an amount from about 0.01 μg/gm to about 50 μg/gm of the composition, and may be administered to humans in dosages of from about 0.01 μg/day to about 100 μg/day and preferably from about 0.1 μg/day to about 10 μg/day in humans.

The compound (2MD) of the invention is also especially suited for treatment and prophylaxis of human disorders which are characterized by an imbalance in the immune system, e.g. in autoimmune diseases, including multiple sclerosis, diabetes mellitus, host versus graft reaction, and rejection of transplants; and additionally for the treatment and prophylaxis of inflammatory diseases, such as rheumatoid arthritis, as well as the improvement of bone fracture healing and improved bone grafts. Acne, alopecia, skin conditions such as dry skin (lack of dermal hydration), undue skin slackness (insufficient skin firmness), insufficient sebum secretion and wrinkles, and hypertension are other conditions which may be treated with the compound (2MD) of the invention.

2MD is also characterized by high cell differentiation activity. Thus, 2MD also provides a therapeutic agent for the treatment of psoriasis, or as an anti-cancer agent, especially against neuroblastoma, retinoblastoma, melanoma, leukemia, colon cancer, breast cancer and prostate cancer. The compound may be present in a composition to treat psoriasis and/or the above referred to cancers in an amount from about 0.01 μg/gm to about 50 μg/gm of the composition, and may be administered topically, transdermally, orally or parenterally in dosages of from about 0.01 μg/day to about 100 μg/day, and preferably from about 0.1 μg/day to about 10 μg/day in humans.

It has also been discovered that 2MD increases breaking strength (cortical strength) as well as crushing strength (trabecular strength) of bones. In accordance with the above finding, one embodiment of the present invention is a method of increasing the strength of a bone comprising administering to a subject an effective amount of 2MD. Thus, 2MD could also be used in conjunction with bone replacement procedures such as hip replacements, knee replacements, and the like. 2MD may also be applied directly on bone by injection in suitable carriers. In addition, 2MD could be used by athletes requiring strong skeletons such as runners (both long distance runners such as cross-country and marathon runners as well as sprinters), weightlifters, discus and hammer throwers, soccer players, tennis players, football players, baseball players, as well as other athletes. Such athletes could be administered 2MD to build bone mass and increase bone strength to thereby inhibit and/or minimize the risk of bone fractures that may occur as a result of playing their chosen sport. Preferably both the athletes and those having bone replacement procedures are individuals that are not afflicted with or have not been diagnosed with a metabolic bone disease.

In accordance with another embodiment, the present invention provides a method for prophylaxis of a disease or disorder characterized by a need to increase the strength of a bone comprising administering to a subject an effective amount of 2MD. Thus, 2MD could be used to build up bone mass and increase bone strength of individuals with normal bone mass and strength (as measured from and compared to base line bone mineral content (BMC) and/or bone mineral density (MBD) readings) so that they can sustain the later loss of bone caused by various diseases or disorders of the bone without incurring fractures. Individuals could be administered 2MD throughout their lifetime (e.g. childhood, adolescence, young adulthood and mature adulthood) or any portion thereof, to develop increased bone mass and strength. Preferably, at the time of administration such individuals are not afflicted with or have not been diagnosed with a metabolic bone disease. Thus, upon onset of osteoporosis induced by hormone deficiency (e.g. postmenopausal osteoporosis in women), or old age (senile osteoporosis in men and women) or drug therapy (e.g. steroid induced osteoporosis as a result of treatment with anti-inflammatory glucocorticoid drugs) or the development of low bone turnover osteoporosis, individuals that have built up their bone mass could sustain the loss of bone caused thereby. In addition to osteoporosis, other circumstances where 2MD could be used as a prophylaxis method include treatment of amenorrheic females usually female athletes, athletes and workers requiring strong skeletons, horses especially race horses (in dosages of about 0.01 μg/day to about 700 μg/day), and astronauts under weightless conditions. It may also be applicable in agriculture for laying hens (in dosages of about 0.0001 μg/day to about 4 μg/day), cows especially lactating cows (in dosages of about 0.01 μg/day to about 550 μg/day), and pigs especially sows being used for rapid farrowing (in dosages of about 0.005 μg/day to about 225 μg/day). The elderly could benefit from an early drug intervention or prophylaxis program for the prevention of bone fractures. Preferably, however, the present invention is directed toward a method for prophylaxis of osteoporosis, especially postmenopausal osteoporosis, comprising administering to a subject prior to menopause an effective amount of 2MD to increase bone mass.

DETAILED DESCRIPTION OF THE INVENTION 2-methylene-19-nor-20(S)-1α,25-dihydroxyvitamin $D_3$ (referred to herein as 2MD) was synthesized and tested. Structurally, this 19-nor analog is characterized by the general formula I previously illustrated herein.

The preparation of 2-methylene-19-nor-20(S)-1α,25-dihydroxyvitamin $D_3$ having the basic structure I can be accomplished by a common general method, i.e. the condensation of a bicyclic Windaus-Grundmann type ketone II with the allylic phosphine oxide III to the corresponding 2-methylene-19-nor-vitamin D analog IV followed by deprotection at C-1 and C-3 in the latter compound:

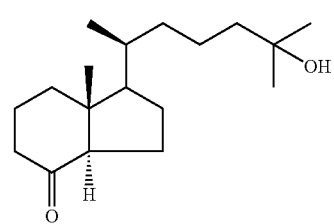

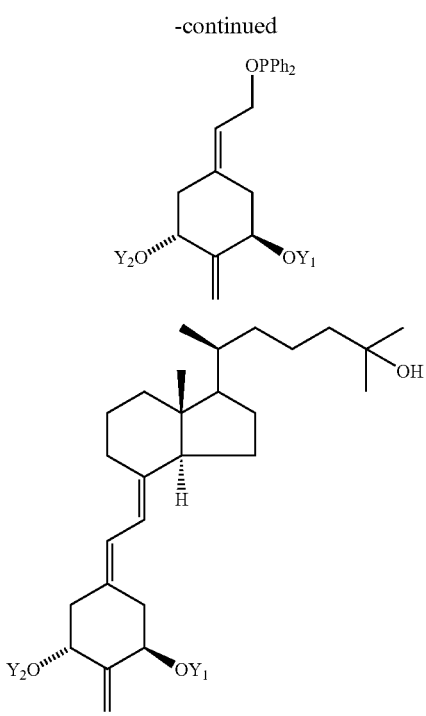

In the structures II, III, and IV groups $Y_1$ and $Y_2$ are hydroxy-protecting groups, it being also understood that any functionalities that might be sensitive, or that interfere with the condensation reaction, be suitably protected as is well-known in the art. The process shown above represents an application of the convergent synthesis concept, which has been applied effectively for the preparation of vitamin D compounds (e.g. Lythgoe et al., J. Chem. Soc. Perkin Trans. I, 590 (1978); Lythgoe, Chem. Soc. Rev. 9, 449 (1983); Toh et al., J. Org. Chem. 48, 1414 (1983); Baggiolini et al., J. Org. Chem. 51, 3098 (1986); Sardina et al., J. Org. Chem. 51, 1264 (1986); J. Org. Chem. 51, 1269 (1986); DeLuca et al., U.S. Pat. No. 5,086,191; DeLuca et al., U.S. Pat. No. 5,536,713).

Hydrindanones of the general structure II are known, or can be prepared by known methods.

For the preparation of the required phosphine oxides of general structure III, a new synthetic route has been developed starting from a methyl quinicate derivative which is easily obtained from commercial (1R,3R,4S,5R)-(−)-quinic acid as described by Perlman et al., Tetrahedron Lett. 32, 7663 (1991) and DeLuca et al., U.S. Pat. No. 5,086,191.

The overall process of the synthesis of compound I is illustrated and described more completely in U.S. Pat. No. 5,843,928 issued Dec. 1, 1998 and entitled "2-Alkylidene-19-Nor-Vitamin D Compounds" the specification of which is specifically incorporated herein by reference.

BIOLOGICAL ACTIVITY OF 2-METHYLENE-20 (S)-19-NOR-1,25-$(OH)_2D_3$ (FIGS. 1–8)

Figure 1:
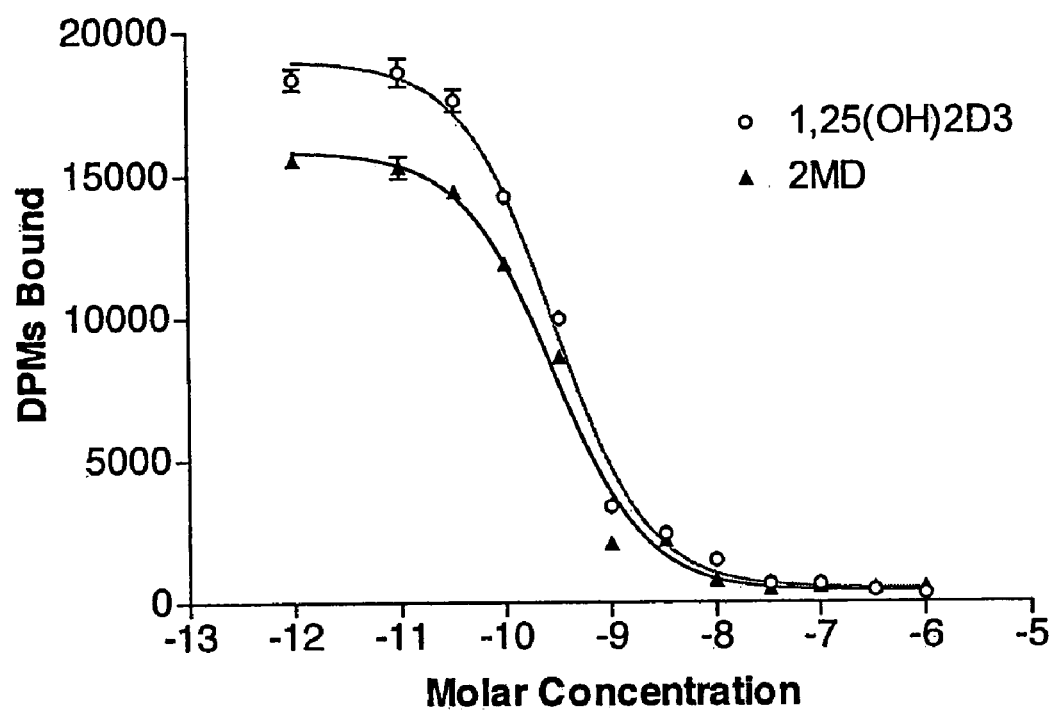
FIG. 1 is a graph illustrating the relative activity of 2-methylene-19-nor-20(S)-1α,25-dihydroxyvitamin $D_3$ (2MD) and 1α,25-dihydroxyvitamin $D_3$ to compete for binding of [$^3$H]-1α,25-(OH)$_2$-$D_3$ to the nuclear vitamin D receptor.

The introduction of a methylene group to the 2-position of the 20(S) isomer of 19-nor-1,25-$(OH)_2D_3$ had little or no effect on binding to the porcine intestinal vitamin D receptor. This compound bound equally well to the full length recombinant rat receptor as compared to the standard 1,25-$(OH)_2D_3$ (FIG. 1). Similar results were found when the native receptor from porcine intestine was studied. It might be expected from these results that this compound would have equivalent biological activity. Surprisingly, however, the 2 methylene and 20(S) substitutions produced a highly selective analog with its primary action on bone.

Figure 2:
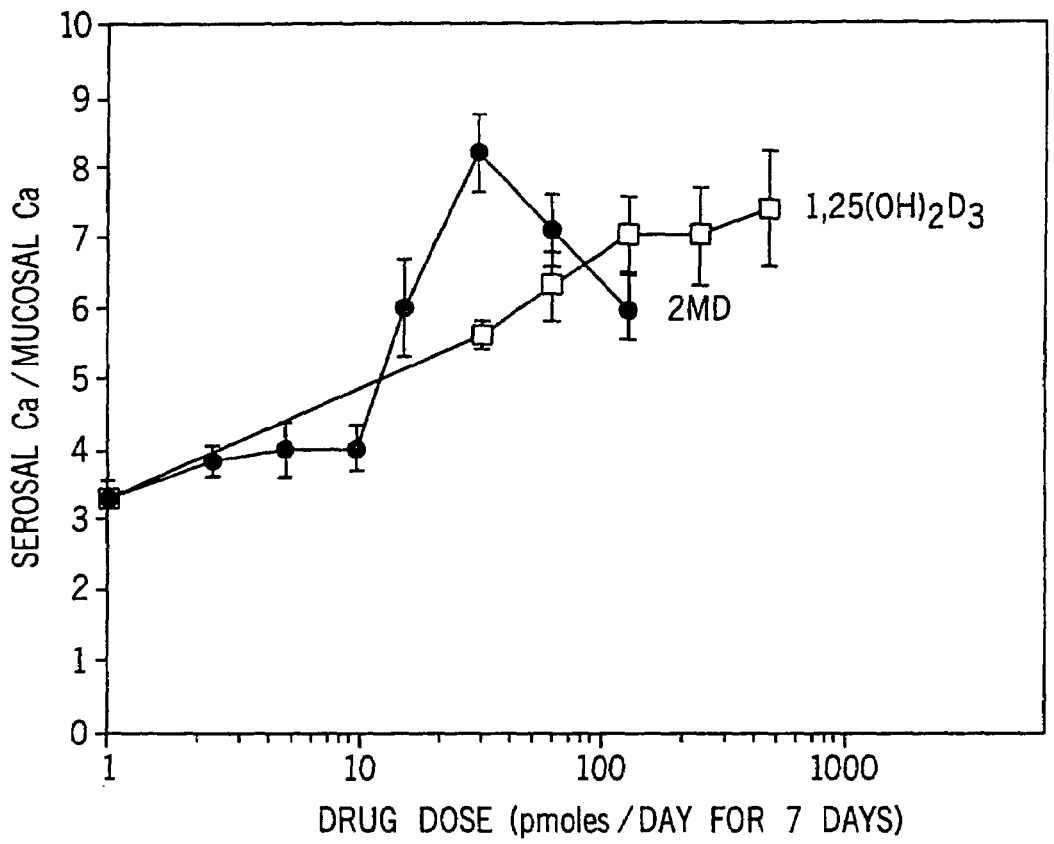
FIG. 2 is a graph illustrating the intestinal calcium transport activity of 2-methylene-19-nor-20(S)-1α,25-dihydroxyvitamin $D_3$ (2MD) as compared to 1α,25-dihydroxyvitamin $D_3$ (1,25-(OH)$_2$D$_3$)

FIG. 2 shows that 2MD has activity similar to that of 1,25-dihydroxyvitamin $D_3$ (1,25$(OH)_2D_3$), the natural hormone, in stimulating intestinal calcium transport in vitamin D-deficient rats given a dose of drug by oral gavage for 7 consecutive days followed by assay using the everted gut sac technique. Values represent means±standard error.

Figure 3:
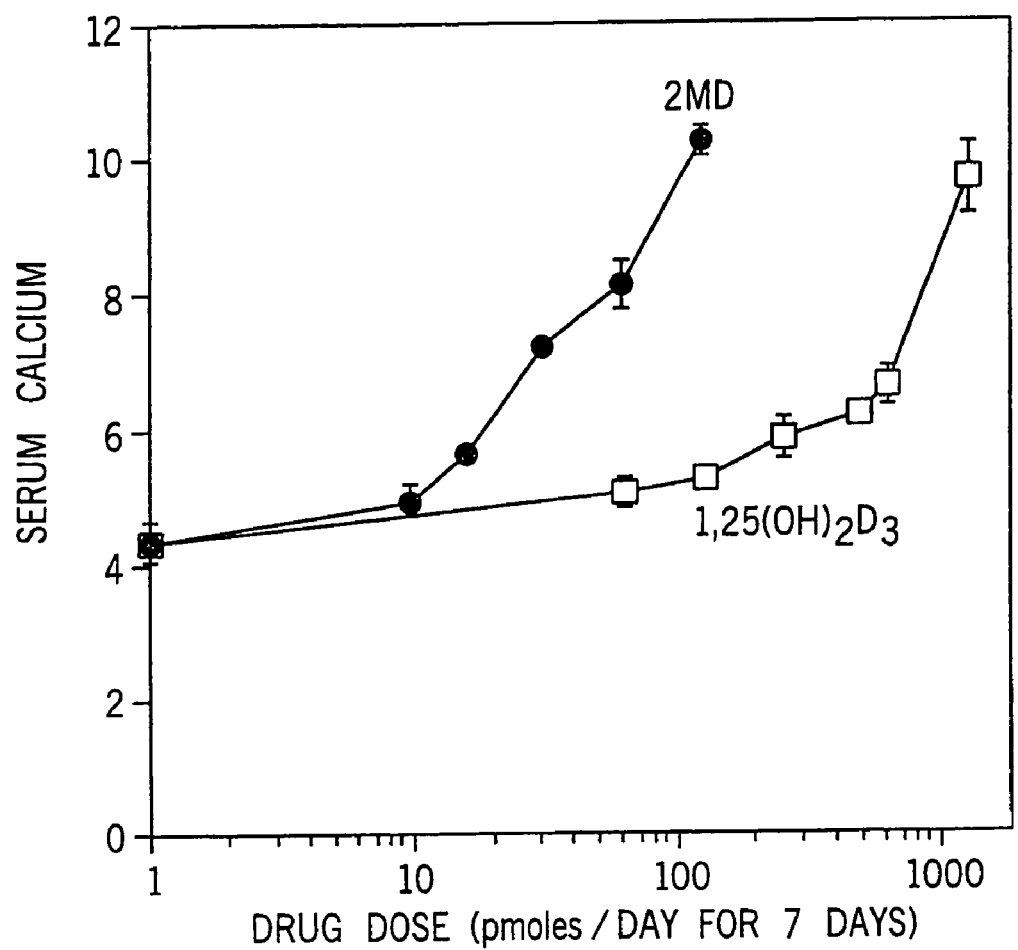
FIG. 3 is a graph illustrating the bone calcium mobilization activity of 2-methylene-19-nor-20(S)-1α,25-dihydroxyvitamin $D_3$ (2MD) as compared to 1α,25-dihydroxyvitamin $D_3$ (1,25-(OH)$_2$D$_3$)

FIG. 3 clearly demonstrates that 2MD is 100 times more potent than 1,25$(OH)_2D_3$ on bone, i.e. the mobilization of bone calcium. Blood serum calcium was measured 24 hours following the last dose in the rats as described in FIG. 2. Values represent mean±standard error.

Figure 4:
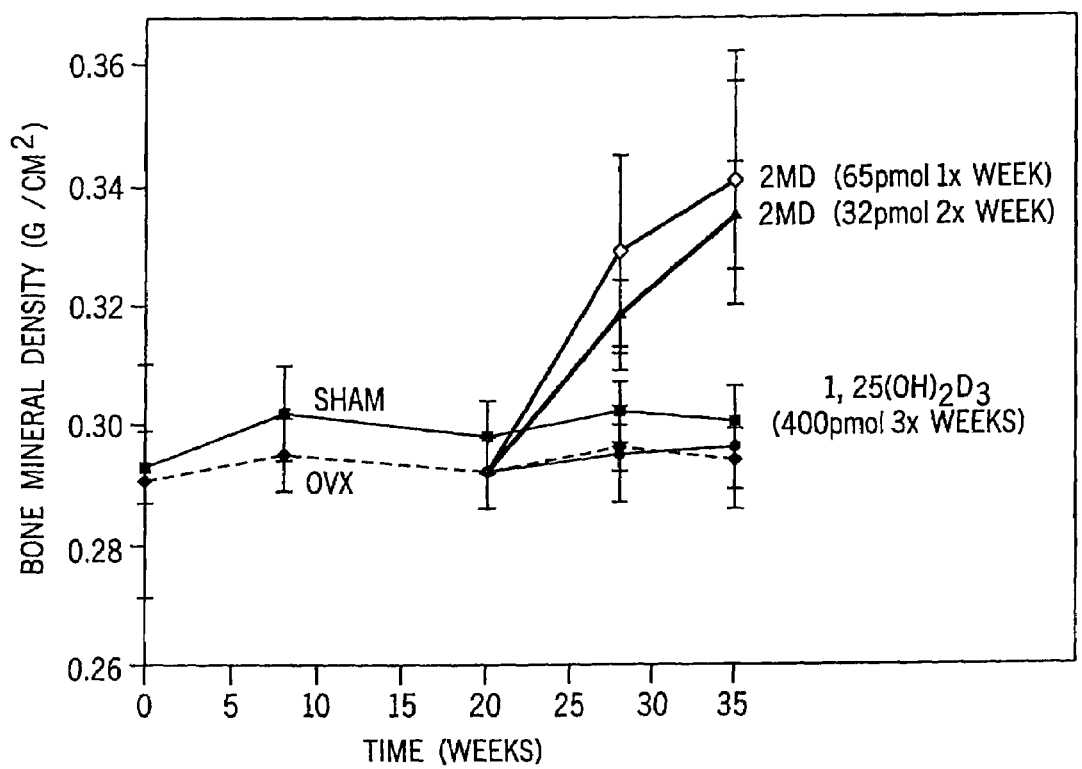
FIG. 4 is a graph illustrating the change in bone mineral density in ovariectomized old female rats as a result of treatment with 2-methylene-19-nor-20(S)-1α,25-dihydroxyvitamin $D_3$ (2MD) as compared to 1α,25-dihydroxyvitamin $D_3$ (1,25-(OH)$_2$D$_3$)

FIG. 4 shows that 2MD is extraordinarily effective in building bone mass in ovariectomized rats as compared to the native hormone without increasing serum calcium concentration (Table 1). This is as yet an unprecedented new finding for a vitamin D compound.

Figure 5:
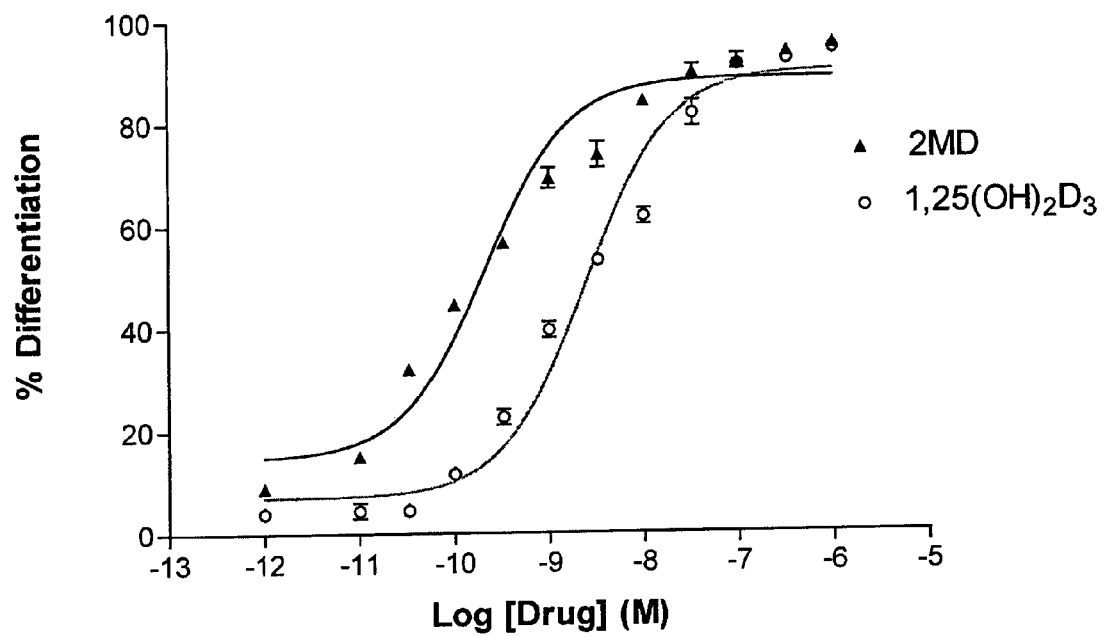
FIG. 5 is a graph illustrating the percent HL-60 cell differentiation as a function of the concentration of 2-methylene-19-nor-20(S)-1α,25-dihydroxyvitamin $D_3$, (2MD) and 1α,25-dihydroxyvitamin $D_3$ (1,25-(OH)$_2$D$_3$)

FIG. 5 illustrates that 2MD is 10–50 times more potent than 1,25$(OH)_2D_3$ on HL-60 cell differentiation, making it an excellent candidate for the treatment of psoriasis and cancer, especially against leukemia, neuroblastoma, retinoblastoma, melanoma, colon cancer, breast cancer and prostate cancer.

Figure 6A:
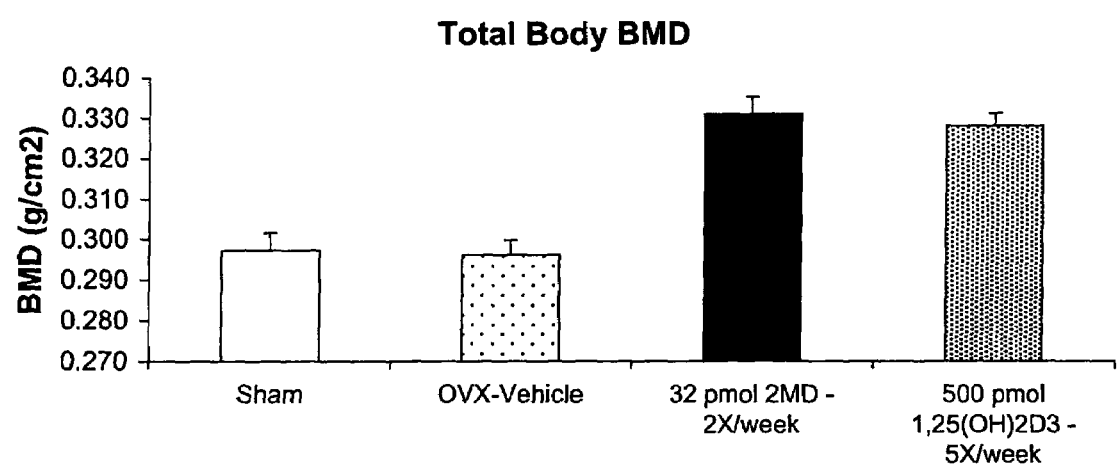
FIG. 6A is a bar graph illustrating the restoration and building of bone in ovariectomized old female rats as a result of treatment with 2-methylene-19-nor-20(S)-1α,25-dihydroxyvitamin $D_3$ (2MD) as compared to 1α,25-dihydroxyvitamin $D_3$ (1,25-(OH)$_2$D$_3$)

Table 1 and FIG. 6A illustrate that 2MD is very effective in increasing bone of ovariectomized, old female rats at 32 pmol given 2 times per week as compared to 1,25$(OH)_2D_3$ given at high doses (250 or 500 pmol) 3 times per week. Note: 2MD also increases % ash in the femur. Values in the figure are mean±standard error.

Figure 6B:
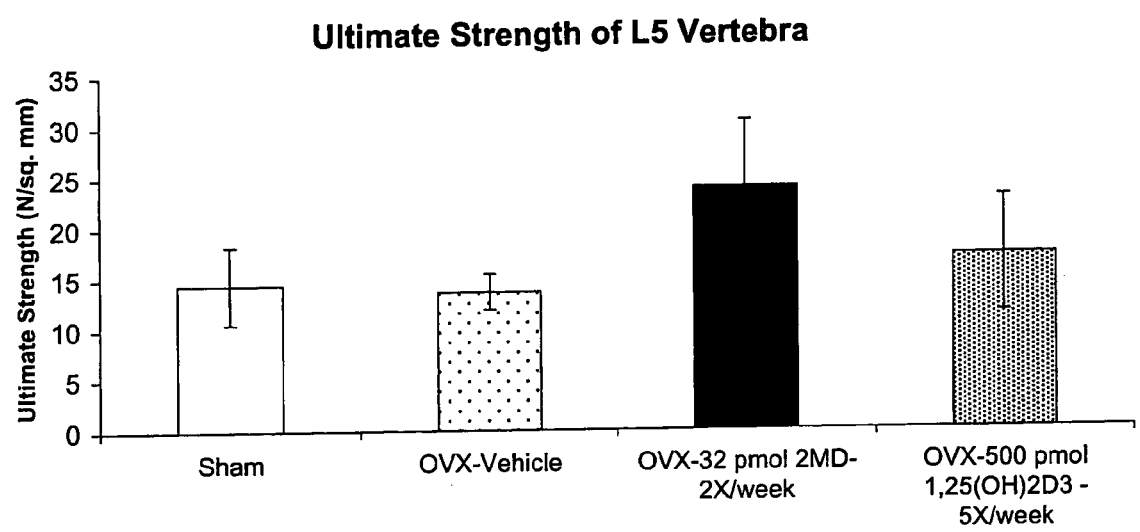
FIG. 6B is a bar graph illustrating the increase of bone strength in ovariectomized old female rats as a result of treatment with 2-methylene-19-nor-20(S)-1α,25-dihydroxyvitamin $D_3$ (2MD) as compared to 1α,25-dihydroxyvitamin $D_3$ (1,25-(OH)$_2$D$_3$)

Table 2 and FIG. 6B show that 2MD increases breaking strength in the femurs (cortical strength) and crushing strength in the vertebra (trabecular strength) of animals shown in Table 1. Values in the figure are mean±standard error.

Figure 7:
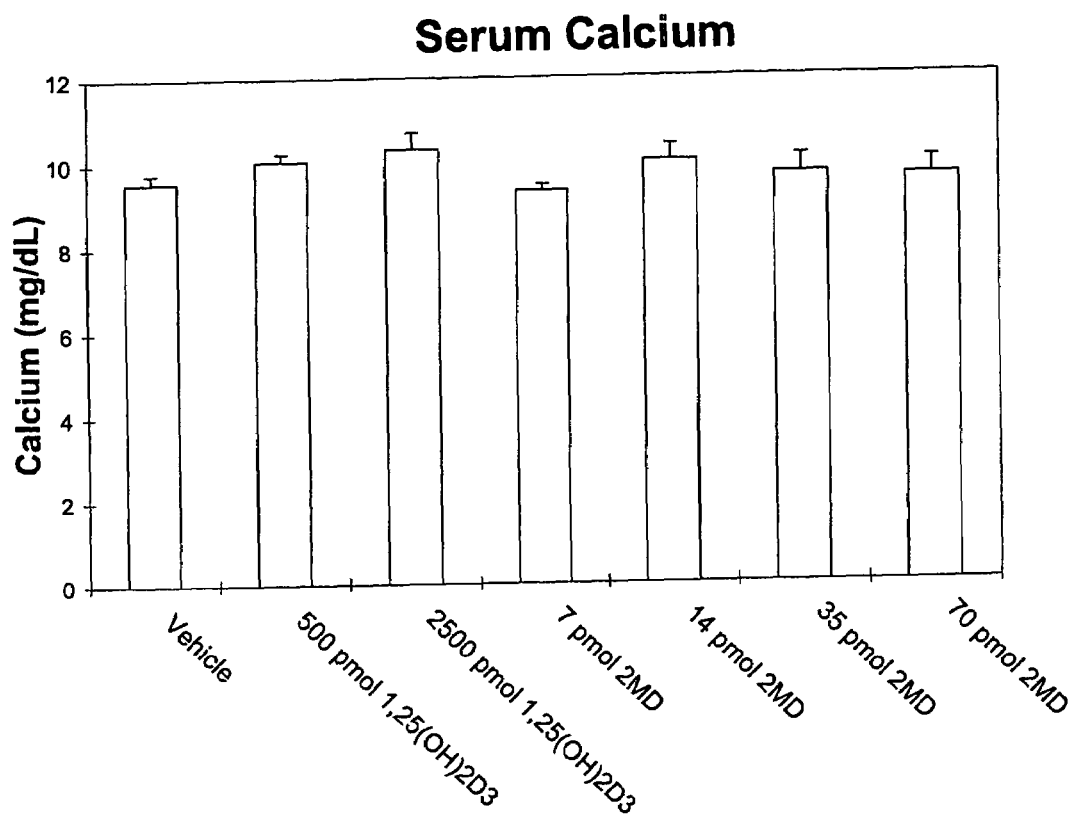
FIG. 7 is a bar graph illustrating blood serum calcium levels in female rats after 6 weeks of treatment at various daily doses of 2-methylene-19-nor-20(S)-1α,25-dihydroxyvitamin $D_3$ (2MD) as compared to 1α,25-dihydroxyvitamin $D_3$ (1,25-(OH)$_2$D$_3$)
Figure 8:
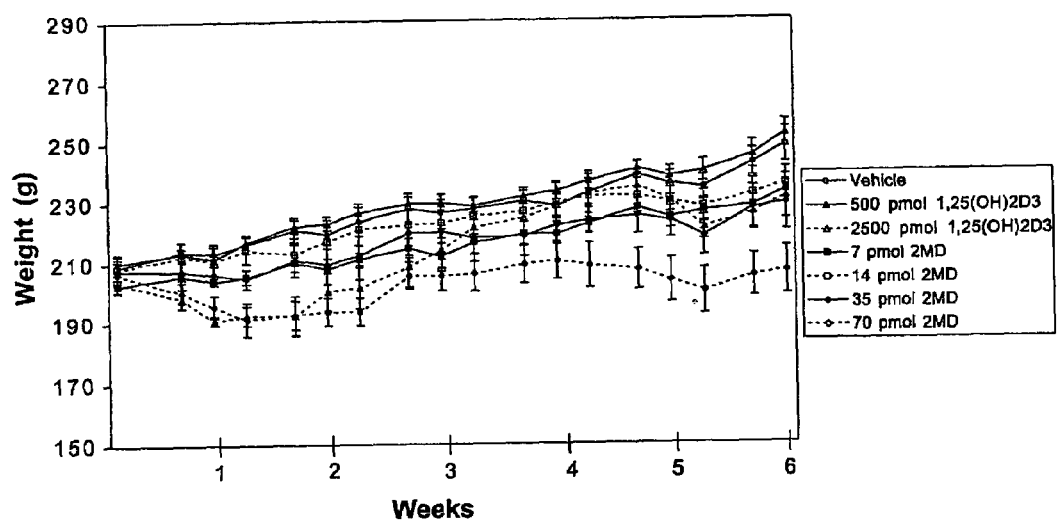
FIG. 8 is a graph illustrating the growth of female rats at various dosages of 2-methylene-19-nor-20(S)-1α,25-dihydroxyvitamin $D_3$ (2MD) as compared to 1α,25-dihydroxyvitamin $D_3$ (1,25-(OH)$_2$D$_3$)
Figure 9:
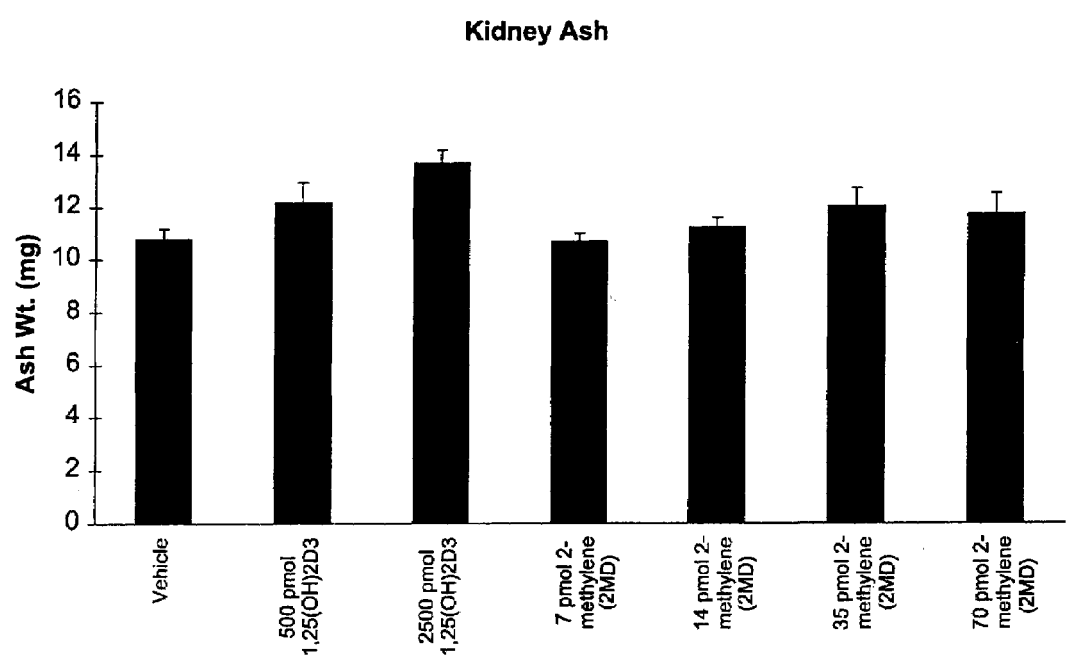
FIG. 9 is a graph illustrating the kidney ash of female rats after 6 weeks of treatment at various daily doses of 2-methylene-19-nor-20(S)-1α,25-dihydroxyvitamin $D_3$ (2MD) as compared to 1α,25-dihydroxyvitamin $D_3$ (1,25-(OH)$_2$D$_3$)
Figure 10:
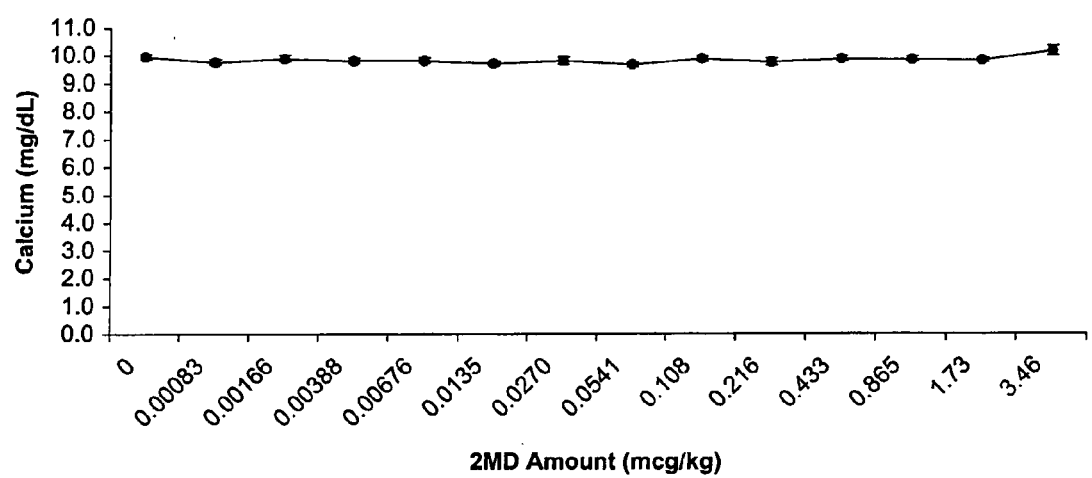
FIG. 10 is a line graph illustrating the blood serum calcium levels 24 hours after dose in Rhesus monkeys given a single oral bolus dose of 2-methylene-19-nor-20(S)-1α,25-dihydroxyvitamin $D_3$ (2MD) at varying concentrations.

FIGS. 7–9 show a six-week toxicity study in rats and demonstrate that 2MD appears safe at up to 35 pmol/day. FIG. 10 shows that in Rhesus monkeys, a single oral dose of 29 μg (1.73 μg/kg) does not cause significant elevation of serum calcium concentration, suggesting even greater safety in primates.

Figure 11:
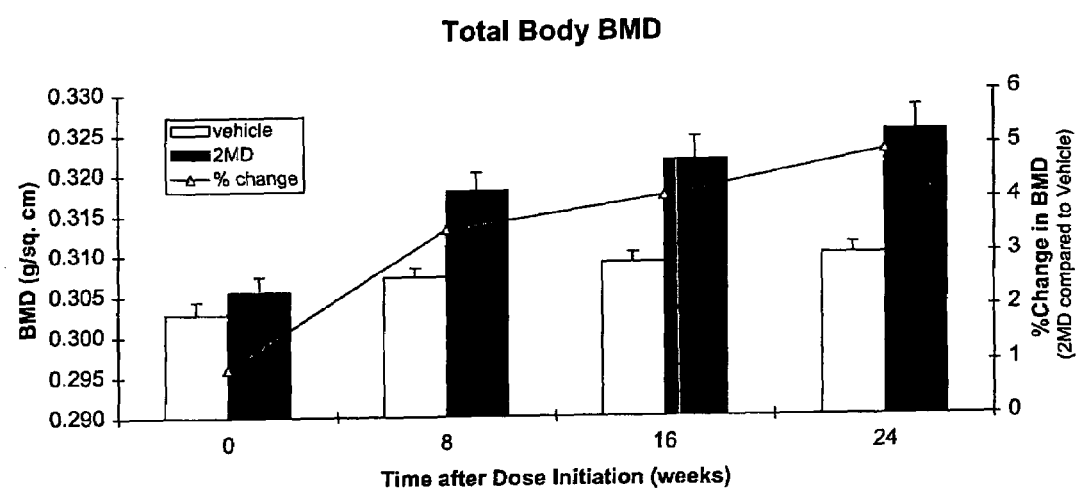
FIG. 11 is a bar graph illustrating the increase in total body bone mineral density (BMD) over time in adult female rats as a result of treatment with 2-methylene-19-nor-20(S)-1α,25-dihydroxyvitamin $D_3$ (2MD, 2.5 ng/kg/day) as compared to control, and which also incorporates a line graph illustrating the percent change in BMD.
Figure 12A:
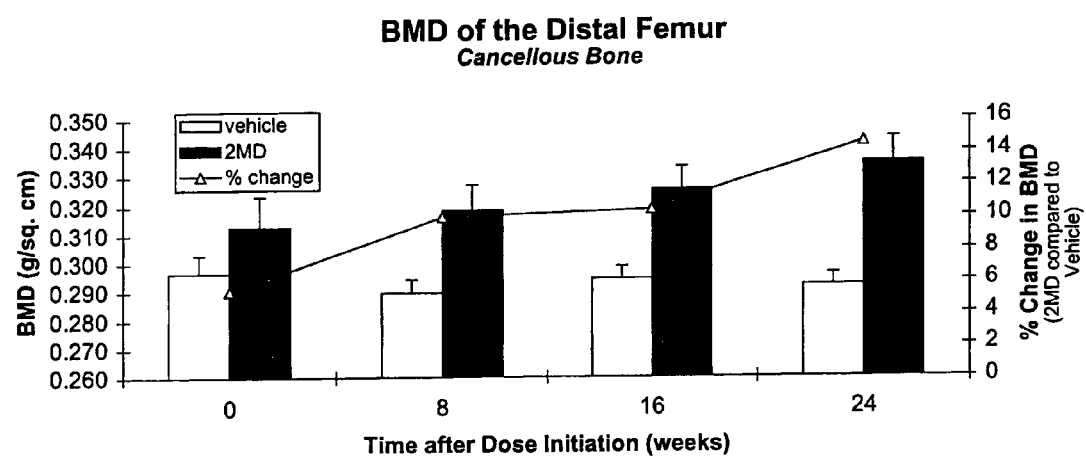
FIG. 12A is a graph illustrating the increase in bone mineral density (BMD) over time in cancellous bone of the adult female rats used to obtain the data for FIG. 11.
Figure 12B:
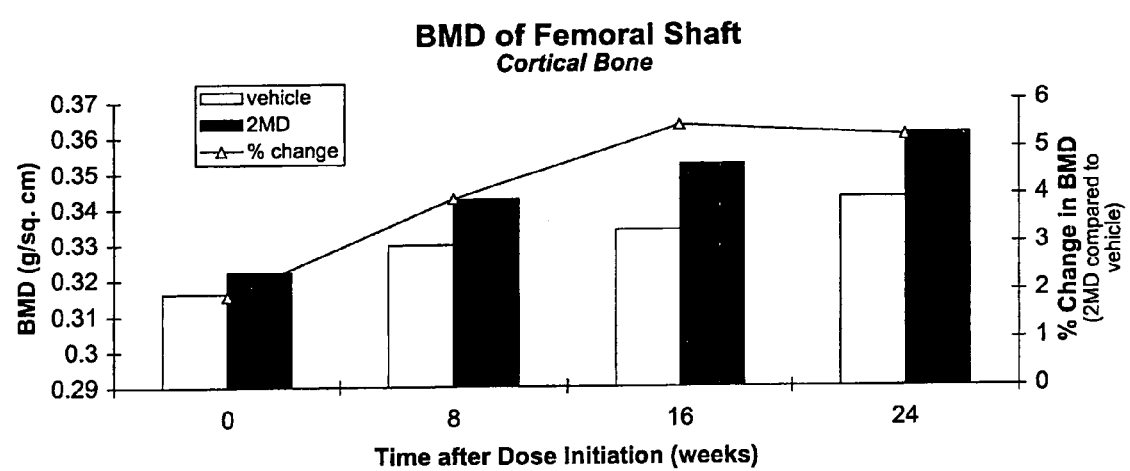
FIG. 12B is a graph illustrating the increase in bone mineral density (BMD) over time in cortical bone of the adult female rats used to obtain the data for FIG. 11.
Figure 13A:
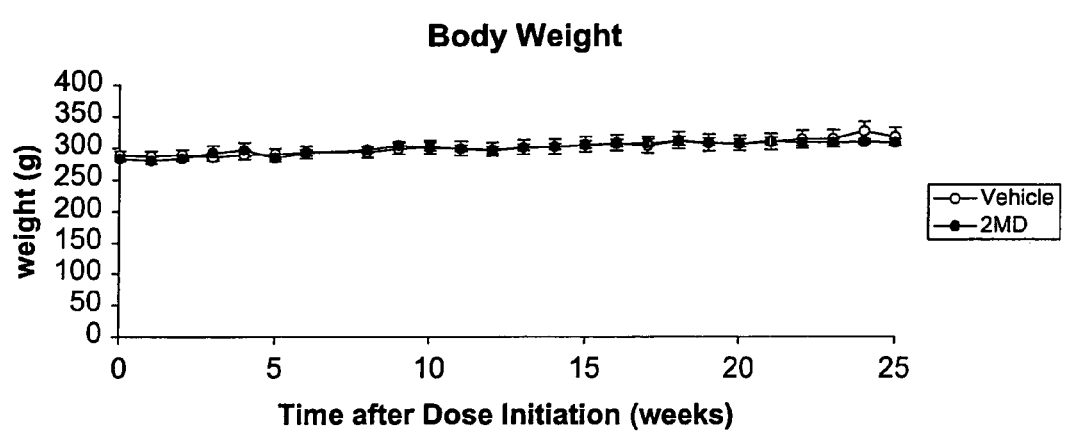
FIG. 13A is a graph illustrating the body weight over time of the adult female rats used to obtain the data for FIG. 11 and FIGS. 12A and 12B.
Figure 13B:
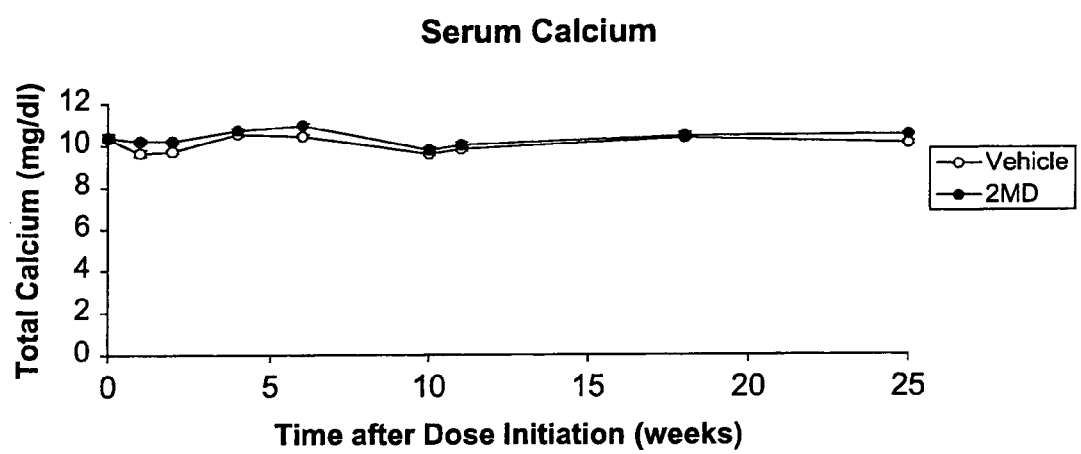
FIG. 13B is a graph illustrating the blood serum calcium levels over time of the adult female rats used to obtain the data for FIG. 11 and FIGS. 12A and 12B.

FIGS. 11, 12A and 12B show that 2MD given at 1.8 pmol/day is highly effective in increasing the bone density in normal adult female rats. Not only does 2MD increase cancellous (trabecular) bone, but it also increases the density of the cortical (shaft) bone as well. FIGS. 13A and 13B show that the remarkable increase in both cortical and cancellous bone are achieved with no adverse effect in either the body weight or serum calcium levels of the animals. Thus, this work shows that 2MD can be safely used not only in ovariectomized animals but also in normal animals at a dose that is effective in increasing bone density.

Competitive binding of the analogs to the porcine intestinal receptor was carried out by the method described by Dame et al. (Biochemistry 25, 4523–4534, 1986).

The differentiation of HL-60 promyelocytic cells into monocytes was determined as described by Ostrem et al. (J. Biol. Chem. 262, 14164–14171, 1987).

The intestinal calcium transport and bone mobilization studies were carried out as described by Sicinski et al. (J. Med. Chem. 41, 4662–4674, 1998) and Suda et al. (J. Nutr. 100, 1049–1052, 1970).

INTERPRETATION OF THE BIOLOGICAL ACTIVITY DATA (FIGS. 1–13)

The in vivo tests of increasing serum calcium of rats on a zero calcium diet provides an insight to osteoblastic or bone activity of 2MD. The dose response curves show that 2MD is at least 80–100 times more potent than 1,25(OH)$_2$D$_3$ in raising calcium in the plasma via the stimulation of the osteoblasts (FIG. 3). At the same time, the activity of 2MD on intestinal calcium transport is approximately equal that of 1,25-(OH)$_2$D$_3$ (FIG. 2). Therefore, these data show 2MD to have selective activity on bone.

2MD is about as active as 1,25(OH)$_2$D$_3$ in binding to the vitamin D receptor (FIG. 1). However, it is between 10–50 times more active than 1,25-(OH)$_2$D$_3$ in causing differentiation of the promyelocyte, HL-60, into the monocyte (FIG. 5). This result suggests that 2MD will be very effective in psoriasis because it has direct cellular activity in causing differentiation and in suppressing growth. It also indicates that it will have significant activity as an anti-cancer agent, especially against leukemia, neuroblastoma, retinoblastoma, melanoma, colon cancer, breast cancer and prostate cancer.

The most important result, however, is that 2MD is extremely effective not only in restoring bone mass of ovariectomized, old female breeder rats as shown in FIGS. 4 and 6 and Tables 1 and 2, but it causes an increase in bone mass above that of sham-operated controls. This illustrates that 2MD is very likely having an anabolic effect on bone or increasing bone formation. Importantly, the increased bone mass provided by 2MD translates into marked increases in bone strength. This increased strength to fracture in femur shows cortical strength while increased strength to crush fractures of vertebra illustrates trabecular (cancellous) bone strength (Table 2 and FIGS. 6A and 6B). Interestingly, even the percent ash is unexpectedly increased further by 2MD. Of great importance is that at the dosage levels used in this study, there was no change in serum calcium in the animals that showed the marked elevation of bone mass. This argues that a window of safety exists between the use of 2MD to increase bone mineral content and the action of 2MD in elevating serum calcium.

Preliminary safety tests carried out on two different occasions have revealed that female rats on a high calcium chow diet tolerate 35 pmol/day of 2MD without elevating serum calcium, reducing body weight or causing mineralization of the kidney (see FIGS. 7–9). Further, preliminary studies in Rhesus monkeys indicates that primates tolerate 2MD extremely well since a dose of as much as 29 μg of this compound was given as a single dose to an 8 kg Rhesus monkey without appreciably elevating serum calcium concentration (FIG. 10). These and other tests indicate that primates will tolerate 2MD extremely well which may give a very large window between efficacy and the danger of hypercalcemia in man.

These results illustrate that 2MD is an excellent candidate for an anti-osteoporosis therapy (both prevention and treatment) and that it may be useful in a number of other circumstances such as autoimmune diseases, cancer, and psoriasis. The studies described in FIGS. 11–13 demonstrate that 2MD can also increase bone mass in normal female rats (see section entitled: "BUILDING BONE MASS OF NORMAL INDIVIDUALS" below).

TABLE 1

Treatment of Ovariectomized Rats with 1,25-(OH)$_2$D$_3$ and 2MD

| Group | Treatment | Treatment Time (Weeks) | BMD (g/cm$^2$) | BMC (g) | Body Wt. (g) | BMC/Body Wt. (mg/g) | Serum CA (mg/dl) | Femur Ash (%) | Femur Ash (mg) |
|---|---|---|---|---|---|---|---|---|---|
| OVX Control | Oil Vehicle/5X/Week | 8 | 0.294 ± 0.004 | 8.64 ± 3.30 | 414 ± 15 | 21.4 ± 1.20 | — | — | — |
| | | 17 | 0.296 ± 0.003 | 9.34 ± 0.50 | 422 ± 19 | 22.3 ± 1.69 | — | — | — |
| | | 30 | 0.296 ± 0.003 | 9.41 ± 0.45 | 404 ± 24 | 23.4 ± 1.60 | 11.1 ± 0.17 | 59.2 ± 0.82 | 386 ± 21.6 |
| Sham Operated | Oil Vehicle/5X/week | 8 | 0.302 ± 0.003 | 9.34 ± 0.38 | 356 ± 14 | 26.3 ± 0.76 | | | |
| | | 17 | 0.300 ± 0.002 | 9.14 ± 0.54 | 351 ± 15 | 26.4 ± 0.82 | | | |
| | | 30 | 0.297 ± 0.004 | 9.20 ± 0.53 | 340 ± 13 | 26.7 ± 1.20 | 11.8 ± 0.20 | 81.5 ± 1.20 | 400 ± 18.0 |
| 1,25(OH)$_2$D$_3$ | 250 pmol/d/5X/Week | 8 | 0.297 ± 0.001 | 8.90 ± 0.40 | 399 ± 9.3 | 22.4 ± 0.48 | | | |
| | | 17 | 0.308 ± 0.008 | 9.6 ± 0.39 | 394 ± 11 | 24.5 ± 0.87 | | | |
| | | 30 | 0.310 ± 0.007 | 10.1 ± 0.30 | 392 ± 16 | 26.1 ± 0.97 | 11.4 ± 0.21 | 60.8 ± 1.1 | 417 ± 23 |
| 1,25(OH)$_2$D$_3$ | 500 pmol/d/5X/Week | 8 | 0.312 ± 0.005 | 10.2 ± 0.40 | 397 ± 14.2 | 26.3 ± 0.57 | | | |
| | 3X/Week | 17 | 0.331 ± 0.008 | 11.5 ± 0.25 | 421 ± 12.8 | 27.6 ± 0.68 | | | |
| | 3X/Week | 30 | 0.328 ± 0.003 | 11.8 ± 0.23 | 432 ± 23.0 | 28.0 ± 0.69 | 11.9 ± 0.20 | 61.4 ± 1.3 | 478 ± 7.5 |
| 2MD | 32 pmol/d/2X/Week | 8 | 0.295 ± 0.009 | 8.4 ± 0.13 | 375 ± 8.2 | 22.4 ± 0.64 | | | |
| | | 17 | 0.313 ± 0.011 | 9.7 ± 0.19 | 373 ± 11.0 | 26.2 ± 0.92 | | | |
| | | 30 | 0.331 ± 0.006 | 11.6 ± 0.40 | 346 ± 11.0 | 33.4 ± 1.60 | 10.8 ± 0.22 | 65.6 ± 1.7 | 462 ± 21.4 |
| 2MD | 65 pmol/d/1X/Week | 8 | 0.293 ± 0.004 | 8.5 ± 0.23 | 408 ± 10.5 | 22.2 ± 0.53 | | | |
| | | 17 | 0.312 ± 0.005 | 9.6 ± 0.24 | 402 ± 11.3 | 24.0 ± 0.80 | | | |
| | | 30 | 0.310 ± 0.009 | 10.2 ± 0.33 | 393 ± 15.0 | 26.0 ± 1.10 | 10.7 ± 0.46 | 62.5 ± 0.57 | 443 ± 11.6 |

All animals were ovariectomized except the sham-operated controls.
Values are expressed as mean ± SEM.

TABLE 2

Strength of Femurs and Vertebrae to Mechanical Stress

| Group | Treatment | Stress Value Femur | Stress Value Vertebra |
|---|---|---|---|
| OVX Control | Oil Vehicle/5X/Week | 109.31 ± 19.60 | 14.26 ± 3.58 |
| Sham-Operated | Oil Vehicle/5X/Week | 121.36 ± 12.5 | 13.67 ± 1.79 |
| 1,25(OH)$_2$D$_3$ | 250 pmol/day/5X/Week | 118.21 ± 19.85 | 19.24 ± 5.66 |
| 1,25(OH)$_2$D$_3$ | 500 pmol/d/3–5X/Week | 116.47 ± 16.20 | 17.14 ± 0.52 |
| 2MD | 32 pmol/d/2X/Week | 134.84 ± 14.12 | 23.93 ± 6.59 |
| 2MD | 65 pmol/d/1X/Week | 133.71 ± 14.06 | 17.07 ± 5.73 |

BUILDING BONE MASS OF NORMAL INDIVIDUALS

Goal: Determine if young adult female rats respond to the anabolic agent, 2MD, by increasing BMD.

Experimental Design:

Animals

All 7-month old, nulliparous female, Sprague-Dawley rats (Harlan Sprague-Dawley, Madison, Wis.) were sham-operated at 7 months of age.

Diet

Beginning with arrival in the facility, rats were fed a purified rodent diet ("Diet 11") prepared in-house (Suda et al, 1970, J. Nutr., 100:1049–1052) and containing 0.47% calcium, 0.3% phosphorus and 1.6 IU vitamin $D_3$/g. To maintain consistent body weights (monitored weekly), rats were fed a total of 150 g diet/week, i.e. 21.5 g/day/rat.

| Compounds | | |
|---|---|---|
| Compound | Source | Lot |
| Vehicle (Neobee M-5 Oil) | Spectrum, New Brunswick, NJ | SN0332 |
| 2MD | Tetrionics, Madison, WI | 010745111 |

| Dosing Regimen | | |
|---|---|---|
| Group | Dose | Animal Number |
| SHAM + vehicle | Vehicle | 10 |
| SHAM + 2MD | 2.5 ng/kg/d | 9 |

Rats were dosed daily beginning 5–6 weeks post-surgery. Neobee oil (vehicle) or 2MD were delivered to the back of the tongue in 100 µL. The dosing solution concentrations were adjusted monthly based on group-average body weights.

Serum Calcium Analyses

At predose and at 1, 2, 4, 6, 10, 11, 18 and 25 weeks after dose, blood was collected 24 hr. after the most recent dose from the tail artery of ether-anesthetized rats. Serum was diluted in 0.1% lanthum chloride and the concentration of calcium determined by atomic absorption spectrometry. The values shown are averages for all rats, and include standard errors.

Bone Mineral Density (BMD) Determinations

Both total body BMD and appendicular (right distal and proximal femur) BMD were determined by dual-energy X-ray absorptiometry (Lunar DPXα-Madison, Wis.; Small Animal Software-version 1.0e) at weeks 0, 8, 16, and 24. Appendicular BMD was performed as described (Haffa et al, 2000, J. Bone Min. Res. 15:872). The values shown are averages for all rats and include standard errors.

Results:

Total body BMD increased above vehicle-control animals in adult female rats given the 2MD orally (FIG. 11). This increase was observed as soon as eight weeks and continued over the course of 24 weeks. Increases in cancellous bone BMD were the most pronounced, with an increase of 14% observed after 24 weeks in rats given 2MD (FIG. 12A). Cortical bone BMD also increased in similar fashion to that observed for the total body (FIG. 12B). These positive effects of 2MD occurred in the absence of any change in body weight (FIG. 13A) or any change in serum calcium (FIG. 13B).

Conclusion:

2MD is obviously effective in increasing bone mass of intact normal female rats. By "normal" it is meant a subject that is not afflicted with or has not been diagnosed with a metabolic bone disease or any other disease/disorder that results in a decrease over time of bone mass. Further, 2MD increases both cancellous (14%) and cortical (6%) bone. Because it has been previously demonstrated that 2MD acts anabolically on bone, it is believed that 2MD may be used to increase bone mass of normal healthy children, adolescents, young adults and/or mature adults. This would result in skeleton that would survive the bone loss of aging and the menopause. In that sense, it can be used as a prophylaxis or preventative measure against fractures resulting from the bone loss of metabolic bone diseases, especially osteoporosis. In addition to osteoporosis, circumstances where 2MD could be used as a prophylaxis method include treatment of amenorrheic females. Furthermore, 2MD could be used in normal subjects when high bone mass is desired, such as athletes. It is envisioned that 2MD can be used to increase bone mass of horses especially race horses and in astronauts preparing for a long journey under weightless conditions. It may also be applicable in agriculture for preventing and/or reducing bone fractures as well as increasing eggshell strength in laying hens, preventing and/or reducing bone fractures in cows especially lactating cows, and preventing and/or reducing bone fractures in pigs especially sows being used for rapid farrowing. Typical commercially significant laying hens include chickens, turkeys, ducks, geese, pheasants, grouse, ostrich and quail.

For treatment purposes, the compound of this invention (2MD) defined by formula I may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compound 2MD may be administered orally, topically, parenterally or transdermally. The compound 2MD is advantageously administered by injection or by intravenous infusion or suitable sterile solutions, or in the form of liquid or solid doses via the alimentary canal, or in the form of creams, ointments, patches, or similar vehicles suitable for transdermal applications. Doses of from about 0.01 µg per day to about 100 µg per day, preferably from about 0.1 µg per day to about 10 µg per day of the compound 2MD are appropriate for treatment purposes in humans, such doses being adjusted according to the disease to be prevented or treated, its severity and the response of the subject as is well understood in the art. Doses of from about 0.0001 µg per day to about 700 µg per day of the compound 2MD are appropriate for treatment purposes in animals. Since the compound exhibits specificity of action, each may be suitably administered alone, or together with graded doses of another active vitamin D compound—e.g. 1α-hydroxyvitamin $D_2$ or $D_3$, or 1α,25-dihydroxyvitamin $D_3$—in situations where different degrees of cell differentiation, bone mineral mobilization and/or calcium transport stimulation is found to be advantageous.

Compositions for use in the above-mentioned treatment and/or prophylaxis of humans or animals aimed at maintaining or increasing bone mass or in other applications such as psoriasis and other malignancies comprise an effective amount of the 2-methylene-20(S)-19-nor-vitamin D compound as defined by the above formula I as the active ingredient, and a suitable carrier. An effective amount of such compound for use in accordance with this invention is from about 0.01 µg to about 50 µg per gram of composition, and may be administered topically, transdermally, orally or parenterally in dosages of from about 0.01 µg per day to about 100 µg per day in humans, and preferably from about 0.1 µg per day to about 10 µg per day in humans. In animals, an effective amount of such compound for use in accordance with this invention is from about 0.01 µg to about 50 µg per gm of composition, and may be administered topically, transdermally, orally or parenterally in dosages of from about 0.0001 µg per day to about 700 µg per day.

The compound 2MD may be formulated as creams, lotions, ointments, topical patches, pills, capsules or tablets, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compound 2MD is advantageously administered in amounts sufficient to effect the differentiation of promyelocytes to normal macrophages, and/or in amounts needed to prevent bone loss, maintain bone mass or increase bone mass. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for injection comprise a sterile oily or aqueous preparation, or a suspension or conjugate of the active ingredient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

We claim:

1. A method for prophylaxis of osteoporosis comprising administering to a subject an effective amount of 2-methylene-19-nor-20(S)-1α,25-dihydroxyvitamin $D_3$ having the formula:

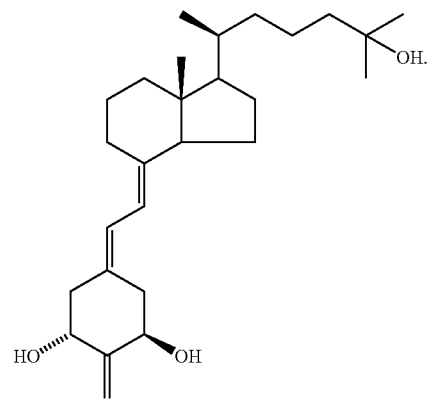

2. The method of claim 1 wherein 2-methylene-19-nor-20(S)-1α,25-dihydroxyvitamin $D_3$ is administered orally.

3. The method of claim 1 wherein 2-methylene-19-nor-20(S)-1α,25-dihydroxyvitamin $D_3$ is administered parenterally.

4. The method of claim 1 wherein 2-methylene-19-nor-20(S)-1α,25-dihydroxyvitamin $D_3$ is administered transdermally.

5. The method of claim 1 wherein said osteoporosis is low bone turnover osteoporosis.

6. The method of claim 1 wherein said osteoporosis is steroid induced osteoporosis.

7. The method of claim 1 wherein said osteoporosis is senile osteoporosis.

8. The method of claim 1 wherein said osteoporosis is postmenopausal osteoporosis.

9. The method of claim 1 wherein 2-methylene-19-nor-20(S)-1α,25-dihydroxyvitamin $D_3$ is administered to a human in a dosage of from about 0.01 µg to about 100 µg per day.

10. The method of claim 1 wherein 2-methylene-19-nor-20(S)-1α,25-dihydroxyvitamin $D_3$ is administered to a human in a dosage of from about 0.1 µg to about 10 µg per day.

11. The method of claim 1 wherein 2-methylene-19-nor-20(S)-1α,25-dihydroxyvitamin $D_3$ is administered to an animal in a dosage of from about 0.000 1 µg to about 700 µg per day.

* * * * *